United States Patent [19]

Frensch et al.

[11] 4,046,906

[45] Sept. 6, 1977

[54] SALTS OF ALKYL 2-BENZIMIDAZOLE-CARBAMATE

[75] Inventors: Heinz Frensch, Frankfurt am Main; Konrad Albrecht, Fischbach, Taunus; Kurt Hartel, Hofheim, Taunus, all of Germany

[73] Assignee: Hoechst Aktiengesellschaft, Frankfurt am Main, Germany

[21] Appl. No.: 618,571

[22] Filed: Oct. 1, 1975

Related U.S. Application Data

[63] Continuation of Ser. No. 462,124, April 18, 1974, abandoned.

[30] Foreign Application Priority Data

Apr. 21, 1973 Germany .............................. 2320529

[51] Int. Cl.$^2$ .................. A61K 31/415; C07D 235/32
[52] U.S. Cl. ................................ 424/273 R; 548/329

[58] Field of Search ...................... 260/309.2; 424/273

[56] References Cited

U.S. PATENT DOCUMENTS

| 3,574,845 | 4/1971 | Actor et al. ........................ 260/309.2 |
| 3,586,670 | 6/1971 | Brenneisen et al. ............... 260/309.2 |

FOREIGN PATENT DOCUMENTS

| 1,195,180 | 6/1970 | United Kingdom .............. 260/309.2 |

*Primary Examiner*—Natalie Trousof
*Attorney, Agent, or Firm*—Curtis, Morris & Safford

[57] ABSTRACT

Salts of benzimidazole-carbamic acid esters with certain organic sulfonic and sulfuric acid esters are substantially insoluble in water and soluble in organic solvents. These are valuable fungicides especially suitable for ultra low volume formulations.

13 Claims, No Drawings

SALTS OF ALKYL 2-BENZIMIDAZOLE-CARBAMATE

This is a continuation of application Ser. No. 462,124 filed Apr. 18, 1974, now abandoned.

Salts of benzimidazole-carbamic acid esters of the general formula

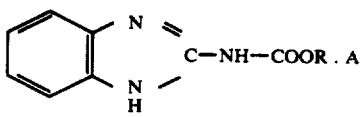

in which R is methyl, ethyl, isopropyl, or sec-butyl and A is an acid having an ionization constant of more than $1.5 \times 10^{-5}$ are known as fungicides (of British Specification No. 1,195,180). The salts of inorganic and organic acids described in said specification are applied in the form of aqueous solutions, optionally in combination with wetting and dispersing agents.

A serious drawback of these salts however is the fact that they are subject to hydrolysis in aqueous solution, whereby the free benzimidazole-carbamates precipitate in the form of crystals and the fungicidal effect is reduced. To prevent hydrolysis further acid must be added to adjust the pH at a value below 3 to 4. The spray liquors are thus highly acidic and, as a consequence, damages to the spraying equipment and to the treatment plants are likely to occur.

It has now been found that salts of benzimidazole-carbamic acid esters with certain organic sulfonic and sulfuric acids avoid these disadvantages by being substantially insoluble in water and therefore not subject to hydrolysis in an aqueous medium.

Subject of the present invention is therefore adducts (salts) of benzimidazole-carbamic acid esters and organic sulfonic and sulfuric acids of the formula

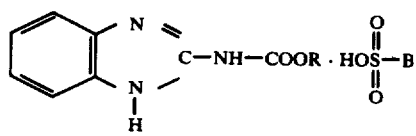

in which R is alkyl having 1 to 4 carbon atoms and B is alkyl, alkenyl or alkoxy each having at least 8 carbon atoms, or alkylphenyl, alkylnaphthyl, or alkoxy phenyl having at least 9 carbon atoms in all.

The compounds of formula II are obtained by reacting a benzimidazole-carbamic acid ester of the formula

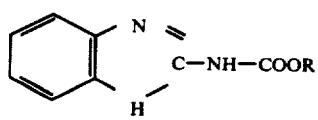

with a sulfuric or sulfonic acid derivative of the formula

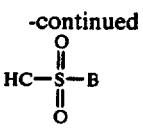

The reaction can be performed either in a solvent or by simply melting together the compounds of formulae III and IV. To avoid decomposition the reaction temperature should not exceed 200° C, preferably 150° C. In general, the reaction temperature is in the range from 0° to +140° C, preferably +20° to +120° C, depending on the solubility in the solvent used. The reaction is expediently carried out at a temperature up to or especially at the boiling point of the solvent used, although it is likewise possible to operate at elevated pressure in a suitable apparatus. If the adduct salt has a melting point below 140° C, preferably at 120° C or even lower the compounds of formula II are preferably prepared by melting together compounds III and IV. The required reaction temperature in this case ranges between the melting point of the acid of formula IV and the melting point of the adduct, which latter should be reached or exceeded at least towards the end of the reaction. To avoid decomposition of the reaction product, its melting point should be exceeded by no more than 20° C.

Suitable solvents to carry out the reaction according to the invention are all those in which at least one of the components III or IV or the final product are soluble to a noticeable extent, for example organic solvents such as alcohols, especially lower alcohols such as methanol, ethanol, butanol; lower alkane carboxylic acids such as formic acid, acetic acid, or propionic acid; amides such as dimethyl formamide or diethyl acetamide; chlorinated aliphatic hydrocarbons such as methylene chloride or chloroform; nitriles such as acetonitrile, or ketones such as cyclohexanone or isophorone; aromatic solvents, for example m-xylene, p-xylene, chlorobenzene, o-dichlorobenzene, phthalic acid esters, more particularly phthalic acid diisooctyl ester; or heterocyclic solvents, for example N-methyl-pyrrolidone. To avoid side reactions when ketones are used, it is expedient to add the acid dropwise to a suspension of BCM in the ketone.

The best suited inorganic solvent is water in which the benzimidazole derivative III is preferably dissolved by adding an acid, preferably a strong inorganic acid. By the addition of a sulfonic or sulfuric acid IV, preferably in the form of its aqueous solution or of a water-soluble salt thereof, preferably an alkali metal salt, the adduct is then formed which precipitates in the aqueous medium.

To prepare products of high purity it is preferred to use either clear solutions of the starting components, for example in an aqueous acidic medium and to precipitate the adduct of formula II by mixing the said solutions, or to use organic solvents in which the final product II forms a clear solution, for example methanol. After separation of the excess amount of starting component III the desired product is obtained in known manner, for example by distilling off the solvent or pouring the solution into water.

The starting components III and IV are used in approximately stoichiometric amounts, but in view of the preferred use as fungicides an excess of one of the components, especially the benzimidazole-carbamic acid ester III of up to 10% by weight, preferably up to 5% by weight, is possible without affecting the effectiveness of the product as fungicide.

It is a further object of the present invention to provide fungicidal agents containing compounds of formula II as active ingredient.

These fungicidal agents contain 2 to 95% by weight of compounds of formula II, they are used in the form of known formulations, for example dusting powders, granules, especially wettable powders, emulsion and dispersion concentrates and ULV concentrates.

In the compounds of the formulae I and III R is by way of example a linear or branched $C_1$ to $C_4$ alkyl radical, such as methyl, ethyl, propyl, isopropyl, butyl, sec.butyl, preferably methyl.

Compounds of formula IV are for example long chain alkane sulfonic acids the linear or branched alkyl radical containing at least 8 and preferably up to 25 carbon atoms, such as octane-, nonane-, decane-, dodecane-, tetradecane-, pentadecane-, hexadecane-, octadecane-, eicosane-sulfonic acid and higher alkane-sulfonic acids, the various isomers thereof and isomer mixtures, more particularly mixtures of the alkanesulfonic acids with different numbers of carbon atoms such as are obtained, for example, in the industrial production of alkanesulfonic acid detergents. Alkanesulfonic acids or mixtures thereof having 10 to 20 carbon atoms, preferably 12 to 18 carbon atoms are preferred.

Compounds of formula IV may also be the corresponding alkenesulfonic acids and mixtures thereof, as well as sulfuric acid monoalkyl esters containing the aforesaid alkyl groups, or mixtures thereof.

Further suitable compounds of formula IV are alkylated benzene-sulfonic acids, for example those carrying one to three alkyl radicals, one of which may also be an alkoxy radical, or those which have a second ring condensed to the benzene nucleus, which second ring may also be hydrogenated. The said benzene-sulfonic acids contain at least 9 carbon atoms, preferably 10 to 20 carbon atoms and more preferably 12 to 18 carbon atoms. Representatives of this class of compounds are, for example, the sulfonic acids of 1,2,4-trimethylbenzene, of p-tert.butyl-toluene, of o- and p-diisopropylbenzene, of 1,4-ditert.-butylbenzene, of hexyl-, oxtyl, nonyl-, decyl-, dodecyl- and tetradecylbenzene or higher alkylbenzenes, of 1-methyl-2-hexylbenzene, of 1-hexyl-4-heptylbenzene, of tetrahydronaphthalene or of the various mono- and dimethyltetrahydronaphthalenes, sulfonic acids of naphthalene, of the various methyl- and dimethylnaphthalenes, of the ethyl- and diethyl- and preferably the various diisopropyl-, butyl- and dibutyl-naphthalenes, furthermore sulfonic acids of the various (alkylated) phenol ethers such as phenyl propyl ether, phenyl isopropyl ether, phenyl butyl ether and ethylphenyl ethyl ether, preferably those having at least 12 carbon atoms, for example phenyl hexyl ether, phenyl decyl ether, phenyldodecyl ether or isononylphenyl methyl ether.

The adducts according to the invention differ from the compounds disclosed in British Specification No. 1,195,180 in that they are substantially insoluble in water, and soluble in organic solvents in which BCM is practically insoluble, such as methylene chloride, xylene and methanol.

The adducts according to the invention are themselves excellent emulsifiers, dispersion media and wetting agents. In many cases they can therefore be formulated especially in high concentrations, without the addition of further wetting and dispersing agents to yield stable wettable powders, or without addition of ionic emulsifiers to yield emulsion concentrates.

Wettable powders contain the adducts of the invention in a concentration from 2 to 95%, preferably 60 to 95%, in combination with the usual carrier materials such as synthetic silicic acid, diatomaceous earth, natural silicates, kieselguhr, bentonite, clay, vermiculite, chalk, or titanium dioxide, and optionally a readily hydrolyzing alkali metal salt of a weak acid, for example sodium carbonate, sodium acetate or potassium carbonate, the proportion of the latter amounting to about 2 to 5, preferably 2.5 to 3.5% by weight. In the case of highly concentrated wettable powders (above 90%) the addition of a dispersion media can be dispensed with as the adducts themselves act as dispersion medium as mentioned above. With low concentrations of active ingredient it is recommended to add a dispersion medium, especially with adducts of alkylbenzene-sulfonic acids. Suitable dispersion media are those generally used, for example sodium dinaphthyl-methylene disulfonate and sodium lignin-sulfonate. According to the requirements the concentrations vary between 0.5 and 10%. With the adducts of the higher alkane-sulfonic acids in high concentration (above 90%) wetting agents can also be dispensed with, while an addition of 0.5 to 1.5% is recommended with adducts of alkylbenzene-sulfonic acids. The lower the adduct concentration the higher the amount of wetting agent. Suitable wetting agents are sodium naphthalene-sulfonate, sodium oleyl-methyl-taurate, sodium alkylbenzene-sulfonates, polyglycol ethers of alkyl phenols and fatty alcohols and fatty alcohol sulfonates.

Emulsion concentrates in accordance with the invention contain about 5 to 30% by weight, preferably 10 to 20% by weight of active ingredient. Suitable solvents are, for example dimethyl formamide (DMF), N-methyl-pyrrolidone, high boiling ketones such as cyclohexanone or isophorone, and aromatic mineral oils. An addition of ionic emulsifiers is not necessary because of the emulsifying action of the salts themselves. The addition of a non ionic emulsifier, for example an alkylphenol, fatty alcohol or fatty acid polyglycol either is advantageous. These are added in an amount of from 0.5 to 15% by weight, depending on the concentration of active ingredient.

The adducts (salts) of the invention are especially suitable for the production of ultra-low-volume (ULV) formulations owing to their solubility in organic solvents. Aqueous solutions are unsuited for ULV-application since water would rapidly evaporate during spraying and the dry salts would drift off with the wind.

ULV formulations contain about 5 to 40% of the adducts of the invention, the balance being one or more high boiling solvents, for example DMF, N-methylpyrrolidone, higher boiling ketones such as isophorone, phthalic acid esters, for example the dimethyl-, diethyl-, diisobutyl- or preferably the diisooctyphthalic acid ester, and aromatic mineral oil fractions boiling in the range of from 160° to 240° C.

For seed treatment the adducts of the invention can be used in the form of solutions, preferably in DMF or dimethyl sulfoxide. Owing to their solubility in organic solvents they can further be used as additives to fungicidal paints, for example for underwater coatings, antibluing agents, wood preservatives and textile preservatives.

The compounds of the invention are well tolerated by the plants and have an excellent systemic fungicidal activity which is equal to that of benomyl (1-butyl-carbamoyl)-2-benzimidazole-methylcarbamate) and superior to that of benzimidazole-carbamic acid methyl ester (BCM). Moreover, the novel adducts have excellent dispersing and wetting properties so that considerable amounts of dispersion media can be saved when they are combined in wettable powders with other fungicides, and higher concentrations of active ingredient become possible.

Of the great number of fungi which can be successfully combated with the compounds of the invention the following are listed by way of example: *Cercospora beticola* causing beet leaf spot, *Cercospora musae* causing Sigatoka disease of bananas, *Penicillium italicum* causing blue mold of citrus fruits, *Penicillium digitatum* causing green mold of citrus fruits, *Cercosporella herpotrichoides* causing eyespot of cereals, *Erysiphe graminis* causing powdery mildew of wheat, *Erysiphe cichoracearum* causing cucumber mildew, *Uncinula necator* causing powdery mildew of vine, *Podosphaera leucotricha* causing apple mildew and other types of mildew in fruit and vegetable growing and ornamental plants, *Botrytis cinerae* causing grey mold in strawberries, vine, salad, *Septoria apii* causing celery leaf spot, *Piricularia oryzae* causing rice blast, *Uromyces phaseoli* causing bean rust, *Hemileia vastatrix* causing coffee rust, *Puccinia triticina* causing leaf rust of wheat, *Puccinia coronifera* causing crown rust of oats and of other rust diseases in ornamental plants, *Tilletia tritici* causing bunt of wheat, *Ustilago tritici* and *Ustilago avenae* causing smut of wheat and oats, *Venturia inaequalis* causing apple scab, Colletotrichum coffeanum causing coffee berry disease, *Colletotrichum lindemuthianum* causing Anthracnose of beans, *Cladosporium fulvum* causing leaf mold of tomatoes, *Fusarium nivale* causing snow mold of rye and wheat, *Verticillium alboatrum* causing wilt disease in tomatoes, cucumbers, melons, lucerne and other crop plants, *Rhizoctonia solani* causing black root rot in cucumbers, peas, beans and other crop plants.

The following examples illustrate the invention. In the biological examples very dilute spray liquors were used to obtain comparable results (spraying to the dripoff). According to modern spray techniques it is however also possible and advantageous to apply the required amount of active ingredient per hectare using concentrated spray liquors. Thus, in practice, spray liquors containing 0.2 to 20% by weight of active ingredient, preferably 2 to 10% by weight, are advantageously used.

EXAMPLES OF PREPARATION

EXAMPLE 1

Tetradecane-sulfonic acid adduct of 2-methoxycarbonylaminobenzimidazole (BCM)

a. 10 Grams of 50% sulfuric acid were added dropwise while stirring to a solution of 30 grams (0.10 mole) of the sodium salt of n-tetradecane-1-sulfonic acid in 200 cc of methanol. After the addition of 19 grams (0.10 mole) of 2-methoxycarbonylaminobenzimidazole (BCM) the whole was stirred for 3 hours at 40° C. Precipitation with icewater yielded 44 grams (94% of the theory) of BCM-tetradecyl-sulfonate ($C_{14}H_{29}SO_3H$/BCM) as a colorless precipitate. The crude product had a melting point of 118°-120° C.

b. In a two-phase system consisting of 10 grams of 50% sulfuric acid and 200 ml of methylene chloride 30 grams (0.10 mole) of the sodium salt of n-tetradecane-1-sulfonic acid were stirred for 2 hours at 40° C together with 19 grams (0.10 mole) of BCM. After the addition of 200 ml of water and 300 ml of methylene chloride the reaction mixture was suction-filtered whereby 38 grams (81% of theory) of a colorless residue melting at 110° C were obtained. After reprecipitation from methanol/water the product melted at 115°-118° C. When the methylene chloride was evaporated a further 10 grams of residue melting from 100° C on upward were obtained.

EXAMPLE 2

Hexadecane-sulfonic acid adduct of 2-methoxy-carbonylaminobenzimidazole (BCM)

35 Grams (0.11 mole) of sodium n-hexadecane-1-sulfonate were suspended in 100 ml of methanol, 5 grams (0.050 mole) of concentrated sulfuric acid were added dropwise and the whole was stirred for 1 hour. The mixture containing hexadecane-1sulfonic acid and sodium sulfate was evaporated to dryness under reduced pressure, the residue was boiled with reflux for 4 hours with 500 ml of methylene chloride and 19 grams (0.10 mole) of BCM. After concentrating the sodium sulfate was washed out by means of water.

48 Grams (96% of theory) of residue were obtained melting at 127°-129° C.

EXAMPLE 3

Dodecylsulfuric acid adduct of 2-methoxy-carbonylaminobenzimidazole (BCM)

29 Grams of technical grade sodium dodecyl sulfate (max. 0.10 mole) were introduced into a mixture of 200 ml of methanol and 5 grams of concentrated sulfuric acid and the whole was stirred for 4 hours at 35°-40° C together with 19 g (0.10 mole) of BCM.

After pouring in water, suction filtration and reprecipitation with methanol/water 35 grams of the desired product were obtained, melting at 135° C.

EXAMPLE 4

($C_{12}$ to $C_{18}$)alkane-sulfonic acid adduct of BCM 303.8 Grams (1 mole, calculated on the mean molecular weight) of a sulfonic acid obtained by sulfoxidation of ($C_{12}$ to $C_{18}$) paraffines and containing 10% of alkane-disulfonic acids were reacted with 210 grams (1.1 mole) of BCM in 200 ml of methanol. After precipitation with icewater the ($C_{12}$ to $C_{18}$)alkane-sulfonic acid adduct of BCM was obtained in a 90% yield besides small proportions of the disulfonic acid adduct. The reaction product melted at 116°-118° C.

In the alkanesulfonic acid mixture used for the reaction the proportions of alkyl radicals were as follows:

| | | | |
|---|---|---|---|
| $C_{11}$ | 0.1 % | $C_{15}$ | 29.7 % |
| $C_{12}$ | 0.5 % | $C_{16}$ | 23.5 % |
| $C_{13}$ | 4.6 % | $C_{17}$ | 13.0 % |
| $C_{14}$ | 26.9 % | $C_{18}$ | 1.4 % |

EXAMPLE 5

Dodecylbenzene-sulfonic acid adduct of BCM

326 Grams (1 mole) of dodecylbenzene-sulfonic acid (linear type) were dissolved while cooling in 150 ml of methanol, and 191 grams (1 mole) of BCM were gradually added with heating whereby the BCM passed into solution. Upon addition of 1 liter of water the adduct separated in the form of grey crystals, which were filtered off with suction and dried at 50° C under reduced pressure. Yield 512 grams (99% of theory), melting point 155°–157° C.

The corresponding adduct of tetrapropylene-benzenesulfonic acid (branched type) was prepared in an analogous manner. It melted at 158°–160° C.

EXAMPLE 6 a. BCM adduct of dodecylbenzene-sulfonic acid

In a mortar 19 grams (0.10 mole) of BCM and 10 grams (0.1 mole) of 50% sulfuric acid were made into a paste which was diluted with water to 1 liter. The BCM was dissolved by boiling the mixture. At 60° C a solution of 32.6 grams (0.10 mole) of dodecylbenzene-sulfonic acid in 200 ml of water was added dropwise while stirring. A light grey whitish salt precipitated at once.

After washing with a large amount of water and drying at 60° C under reduced pressure the desired BCM-dodecylbenzenesulfonate melting at 156°–158° C was obtained.

b. BCM adduct of p-toluenesulfonic acid (comparative example)

19 Grams (0.10 mole) of BCM and 10 grams of 50% sulfuric acid (0.10 mole) were made into a paste and dissolution was brought about by boiling with 1 liter of water. After cooling to 60° C, 17 grams (0.10 mole) of p-toluenesulfonic acid were added. No precipitate was formed in contradistinction to Example 6a. A precipitate was obtained by adding soda solution to a pH of 2 – 3, which precipitate was not stable to water. When the precipitate was washed with dilute acid the infrared spectrum revealed that it consisted mainly of free BCM (yield in mixture 16 grams only).

By further neutralizing with soda solution to pH 6 pure BCM was obtained, i.e. starting material.

EXAMPLE 7

Tetrahydronaphthalene-2-sulfonic acid adduct of BCM

19 Grams (0.10 mole) of BCM and 10 grams (0.1 mole) of 50% sulfuric acid were made into a paste and disolution was brought about by boiling in 1 liter of water. At 60° C a solution of sodium tetrahydronaphthalene-2-sulfonate (24 grams, 0.10 mole) in 200 ml of water was added dropwise, whereupon a precipitate separated immediately.

17 grams of adduct having a melting point of 225° C were obtained (77% of theory)

EXAMPLE 8

Dibutylnaphthalene-sulfonic acid adduct of BCM 38 Grams (0.20 mole) of BCM and 64 grams (about 0.20 mole) of technical grade dibutylnaphthalene-sulfonic acid in 500 ml of methylene chloride were stirred for 3 hours at 40° C. The mixture was then stirred with active carbon and filtered off with suction. The filtrate was concentrated, yielding a light beige residue melting at 105°–108° C. The yield amounted to 77 grams (75% of theory).

EXAMPLE 9

BCM adduct of 1,2,4-trimethylbenzene-2-sulfonic acid 28.5 Grams (0.15 mole) of BCM were made into a paste with 30 grams (0.15 mole) of 50% sulfuric acid, dissolution was brought about in 1.5 liters of hot water. 47 Grams of 71% technical sodium trimethylbenzene-sulfonate (corresponding to 0.15mmole of pure sulfonate) were dissolved in 200 ml of water and the solution was combined with the BCM solution. With pH control 75 ml of 2 N soda solution (0.15 val) were added dropwise. The precipitated adduct was filtered off with suction. After drying it was soluble in methanol. The yield amounted to 45 grams, corresponding to 77%, calculated on BCM. The product melted at 171°–172° C.

EXAMPLE 10

BCM adduct of octadecyl-sulfuric acid

74 Grams (max. 0.2 mole) of sodium octadecylsulfate $(H(CH_2)_{18}OSO_3Na$ (technical grade), 38 grams (0.2 mole) of BCM and 10 grams (0.2 val) of concentrated sulfuric acid were added while stirring to 400 ml of methanol. After heating the mixture for 5 hours at 40° C, it was stirred into 3.5 liters of water. After standing for 30 minutes the precipitate could be readily filtered off. It was recrystallized from methanol/water.

45 Grams of adduct (56% of theory, calculated on unrecovered BCM) melting at 129°–131° C were obtained.

EXAMPLE 11

0.2 Mole each of sodium decyl sulfate (technical grade), sulfuric acid and BCM were reacted in methanol as described in Example 10. After reprecipitation with methanol/water 51 grams of adduct were obtained, i.e. 69% of theory, calculated on reacted BCM. The adduct melted at 138°–139° C.

EXAMPLE 12

$C_{12}$ to $C_{18}$-alkane-sulfonic acid adduct of BCM

91 Grams (0.30 mole) of ($C_{12}$ to $C_{18}$) alkane-sulfonic acid mixture (technical grade as used in Example 4) were mixed with 100 ml of glacial acetic acid and, while heating to 40° C, 63 grams (0.33 mole) of BCM were introduced. After heating for 3 hours the mixture was stirred into water.

After suction filtration the precipitate was dissolved in cold methanol and reprecipitated with water. 112 Grams of adduct melting at 119°–121° C were obtained, corresponding to 75% of the theory.

EXAMPLE 13

Tridecane-sulfonic acid adduct of BCM

The sodium tridecyl-sulfonate used for the preparation of the adduct was obtained by sulfoxidation of($C_{13}$)-paraffin fraction and contained less than 2% of sulfonic acid groups at the chain end.

20 Grams of sodium tridecyl-sulfonic acid, 3.5 grams of concentrated sulfuric acid and 13.4 grams of BCM were stirred for 4 hours at 40° C in 100 ml of methanol. After pouring into water, suction filtration and reprecipitation from methanol/water 17 grams of adduct melting at 129°–131° C were obtained.

EXAMPLE 14

Decane-sulfonic acid adduct of BCM

The sodium decyl-sulfonate used for preparing the adduct was obtained by sulfoxidation of decane and contained less than 2% of sulfonic acid final groups.

19 Grams of sodium decyl-sulfonate, 4.5 of concentrated sulfuric acid and 13.4 grams of BCM in 100 ml of methanol, were stirred for 4 hours at 40° C. After pouring into water, suction filtration and reprecipitation from methanol/water, 21 grams of adduct melting at 127°–129° C and 2 grams of unreacted BCM were obtained. The IR spectrum showed the characteristic adduct band at 1755 cm$^{-1}$.

EXAMPLE 15

$C_{18}$-olefin-sulfonic acid adduct of BCM

50 Grams of technical grade sodium salt of a $C_{18}$-olefinsulfonic acid mixture (obtained by sulfonation of α-octadecene with $SO_3$), 28 grams of BCM and 8 grams of concentrated sulfuric acid in 300 ml of methanol were stirred for 3 hours at 40° C. After pouring in water, suction filtration and reprecipitation from methanol/water, 31 grams of adduct melting at 75° C were obtained.

EXAMPLE 16

$C_{16}$-olefin-sulfonic acid adduct of BCM

37 Grams of adduct melting at 97°-102° C were obtained in the manner described in Example 15 from 50 grams of technical grade sodium salt of a $C_{16}$-olefin-sulfonic acid mixture (obtained by sulfonation of α-hexadecene with $SO_3$) and 29 grams of BCM.

EXAMPLE 17

BCM adduct of n-dodecylbenzene-sulfonic acid

32 Grams of dodecylbenzene-sulfonic acid and 19 grams of BCM were mixed whereby the temperature spontaneously rose to 45° C. The mixture was slowly heated and then digested for about 10 minutes in an oil bath of 170° C until a homogeneous melt had formed. After solidification the product could be readily pulverized and had a melting point of 135° to 145° C. The crude grey adduct was dissolved in 100 ml of cold methanol, decolorized with active carbon and precipitated with water.

45 Grams of adduct melting at 154°-156° C were obtained, which was identical with the product of Example 6a.

EXAMPLE 18

BCM adduct of p-diisopropylbenzenesulfonic acid

38 Grams of BCM and 48 grams of diisopropylbenzenesulfonic acid were heated for 30 minutes to 130° C. After cooling the melt could be pulverized, the melting point of the crude product being 98°-101° C. The crude product could be reprecipitated from cold methanol/water. It had a melting point of 109° C.

EXAMPLE 19

BCM adduct of p-diisopropyl-benzene-sulfonic acid

162 Grams (1 mole) of p-diisopropylbenzene and 143 grams of 20% oleum were stirred for 4 hours at 120° C (cf. C.A. 60, 15 763d, M. M. Movsumzade and I. K. Magamedov, Azerb.Khim.Zh. (1963) (3), 143).

Upon addition of 20 ml of water the mixture solidified. It was dissolved in 500 ml of methanol and 153 grams (0.8 mole) of BCM were added. After stirring for 4 hours and heating to 40° C the reaction mixture was filtered off through a glass frit and water was added to the filtrate. Grey crystals separated melting at 109° C. The yield amounted to 325 grams (94% of the theory).

EXAMPLE 20

(Comparative example)

Reaction of BCM with n-hexyl-sulfonic acid

19 Grams (0.1 mole) of BCM and 20 grams of 50% sulfuric acid (0.2 val) were made into a paste and dissolution was brought about by boiling in 1 liter of water. 25 Grams (0.133 mole) of sodium n-hexyl-sulfonate dissolved in 100 ml of water were added. A precipitate did not separate. Next, 50 ml of 2N soda solution (0.1 val) were dropped in whereupon the pH rose to 2.1 and a precipitate formed, which was filtered off with suction and washed with acidified water. It was found to be pure BCM.

EXAMPLE 21

BCM adduct of a petroleum sulfonic acid

19 Grams of BCM, 43 grams of the sodium salt of a petroleum sulfonic acid (mean molecular weight 425, medium chain length $C_{23}$) and 7 grams of concentrated sulfuric acid in 1 liter of methanol were heated for 4 hours to 40° C and the reaction mixture was stirred into 3 liters of water. The precipitated product was taken up in methylene chloride, the methylene chloride solution was washed with water, clarified with active carbon and concentrated.

34 Grams of adduct melting at 72°-74° C were obtained.

FORMULATION EXAMPLES

EXAMPLE A

Wettable powder formulation of $C_{12}$ to $C_{18}$ alkane-sulfonic acid-BCM adduct In a disk attrition mill a mixture of 90% by weight of ($C_{12}$ to $C_{18}$)-alkanesulfonic acid adduct of BCM according to Example 4 (corresponding to 35% by weight of BCM),
3% by weight of anhydrous soda
7% by weighrt of synthetic silicic acid was ground at a high speed. The wettable powder obtained was stable to storage and corresponded to CIPAC testing conditions. Residue on a 44 micron sieve was 2%, pH of a 10% aqueous spray liquor was 6.8 to 7.2. After termination of the suspension test in water, the unchanged BCM-adduct could be extracted quantitatively with methylene chloride.

EXAMPLE B

Wettable powder formulation of dodecylbenzene-sulfonic acid-BCM adduct

In a blowing mill a mixture of

94% by weight of dodecylbenzene-sulfonic acid adduct of BCM, corresponding to 35% by weight of BCM
3% by weight of anhydrous soda
1.5% by weight of sodium naphthalene-sulfonate
1.5% by weight of synthetic silicic acid was ground at a high speed and blown through a 0.3 sieve. The suspension properties complied with the requirements. Residue on a 44 micron sieve was 1%. The main quantity of the wettable powder had a particle size in the range of from 5 to 15 microns, the pH of a 10% aqueous spray liquor being 7.5. After termination of the test the adduct could be extracted from the suspension as such, proving that no hydrolysis had taken place.

EXAMPLE C

Wettable powder formulation of dodecylbenzene-sulfonic acid adduct of BCM

In the manner described in Example B a mixture of

81% by weight of dodecylbenzene-sulfonic acid adduct, corresponding to 30% by weight of BCM
5% by weight of sodium dinaphthylmethanesulfonate
2% by weight of partially saponified polyvinyl acetate (70% polyvinyl alcohol)
2% by weight of sodium dibutylnaphthalene-sulfonate
3% by weight of anhydrous soda
1% by weight of polypropylene glycol
6% by weight of synthetic silicic acid was ground and transformed into a wettable powder of like quality.

EXAMPLE D

A formulation of the dodecylbenzene-sulfonic acid adduct of BCM suitable for application by the ULV process was obtained by preparing a solution containing 40% by weight of dodecylbenzene-sulfonic acid adduct of BCM
30% by weight of dimethyl formamide
30% by weight of phthalic acid diisooctyl ester

EXAMPLE E

The following mixture proved likewise suitable as ULV solution

40% by weight of dodecylbenzene-sulfonic acid adduct of BCM
30% by weight of dimethyl formamide
30% by weight of N-methylpyrrolidone

EXAMPLE F

A further ULV mixture consisted of

30% by weight of dodecylbenzene-sulfonic acid adduct of BCM
40% by weight of N-methyl-pyrrolidone
40% by weight of phthalic acid diisooctyl ester

EXAMPLE G

To obtain an emulsion concentrate the following components were used:

10% by weight of dodecylbenzene-sulfonic acid adduct of BCM
30% by weight of cyclohexanone
20% by weight of dimethyl formamide
30% by weight of aromatic mineral oil (boiling range 180°-260° C)
5% by weight of alkylphenol polyglycol ether
5% by weight of castor oil polyglycol ether.

In the concentrations used for application the emulsion concentrate formed a stable milky emulsion in which no crystals of BCM separated after standing for 30 minutes.

EXAMPLE H

In the manner described in Example A the following mixture was ground to a wettable powder in a disk attrition mill or blowing mill with highest speed of the grinding disk:

60% by weight of 2-methoxycarbonylamino-benzimidazolen-tetradecyl-sulfonate
5% by weight of sodium dinaphthyl-methylene-disulfonate (Tamol NNO$^R$)
2% by weight of sodium alkylnaphthalene-sulfonate (Leonil DB$^R$)
2% by weight of partially saponified polyvinyl acetate (Mowiol 70/88$^R$)
1% by weight of polypropylene glycol
3% by weight of calcined soda
16% by weight of powdered skim milk
11% by weight of finely dispersed silicic acid

EXAMPLE I

In the manner described in Example H the following mixture was ground to give a wettable powder:

60% by weight of 2-(methoxycarbonylamino)-benzimidazolelauryl sulfate
5% by weight of sodium dinaphthyl-methylene-disulfonate (Tamol NNO$^R$)
2% by weight of sodium alkyl-naphthalene-sulfonate (Leonil DB$^R$)
2% by weight of partially saponified polyvinyl acetate (Moviol 70/88$^R$)
1% by weight of polypropylene glycol
3% by weight of calcined soda
16% by weight of powdered skim milk
11% by weight of finely dispersed silicic acid

EXAMPLE K

In the manner described in Example H the following components were ground to give a wettable powder:

60% by weight of 2-methoxycarbonyl-amino-benzimidazoledibutyl-naphthalene-1-sulfonate
5% by weight of sodium dinaphthyl-methylene-disulfonate (Tamol NNO$^R$)
2% by weight of sodium alkylnaphthalene-sulfonate (Leonil DB$^R$)
2% by weight of partially saponified polyvinyl acetate (Moviol 70/88$^R$)
1% by weight of polypropylene glycol
3% by weight of calcined soda
16% by weight of powdered skim milk
11% by weight of finely dispersed silicic acid.

BIOLOGICAL EXAMPLES

EXAMPLE I

Apple seedlings of the type EM IX, suitable as grafting base, in the 4 leaf-stage were strongly infested with conidia of apple scab (Fusicladium dendriticum) and the infested plants were placed in a chamber having a temperature of 20° C and a relative humidity of 100%. After 2 days the plants were transferred to a greenhouse having a temperature of 18° C and a relative humidity of 90-95%.

After a time of infection of 6 days, during which the conidia of apple scab could germinate and penetrate into the leaf tissue, the plants were sprayed to the drip off with aqueous suspensions of the wettable powders of Examples A, B, and C.

As comparative agent a wettable powder formulation containing 50% of benomyl (comparative Agent III), a normal formulation of BCM (comparative agent I) and a formulation of BCM hydrochloride (comparative agent II) were used.

The active ingredients were applied in concentrations of 400, 200, 100 and 50 mg per liter of spray liquor.

After drying of the coating containing the active ingredient, the plants were brought again into the greenhouse having optimum infestation conditions and after a time of incubation of 3 weeks the seedlings were examined. The degree of infestation was evaluated by visual inspection; it is expressed in % of infested leaf surface, relative to untreated but infested control plants = 100%.

The test results summarized in Table I show that the compounds of the invention have an excellent fungicidal effect which is equal to that of benomyl and far superior to BCM and its hydrochloride.

TABLE I

| Active compound | % leaf surface infested with Fusicladium with mg of active compound per liter of spray liquor | | | |
|---|---|---|---|---|
| | 400 | 200 | 100 | 50 |
| Ex. A | 0 | 0 | 5 | 10 |
| Ex. B | 0 | 0 | 3 | 12 |
| Ex. C | 0 | 0 | 2 | 8 |
| BCM (I) | 20 | 28 | 35 | 45 |
| BCM-HCl (II) | 0 | 5 | 12 | 25 |
| benomyl (III) | 0 | 0 | 8 | 15 |
| untreated infested plants | 100 | | | |

EXAMPLE II

Cucumber plants in the two leaf stage and after removal of the cotyledons, were treated at the lower side of the leaves only with the wettable powders and comparative agents specified in Example I by means of a microapplicator while the upper sides of the leaves and the stems were covered with filter paper to avoid any contamination by the active ingredients.

The active ingredients were applied in concentrations of 500, 250, 125, 60 and 30 mg per liter of spray liquor.

After drying of the coating containing the active ingredient the upper sides of the leaves were strongly infested with conidia of cucumber mildew (*Erysiphe cichoracearm*) and the plants were placed in a greenhouse at a temperature of 22°-24° and a relative humidity of 80 to 90%.

After an incubation time of 14 days the plants were examined as to their infestation with cucumber mildew. The degree of infestation was evaluated by visual inspection; it is expressed in % of infested leaf surface, relative to untreated infected control plants = 100%.

The result of the test is summarized in Table II. It can be seen that the compounds of the invention have a distinctly better activity than BCM and its hydrochloride and in part are even superior to benomyl.

TABLE II

| Formulation of | % leaf surface infested with cucumber mildew with mg of active compound per liter of liquor | | | | |
|---|---|---|---|---|---|
| | 500 | 250 | 125 | 60 | 30 |
| Example A | 0 | 0 | 3 | 5 | 15 |
| Example B | 0 | 0 | 5 | 5 | 12 |
| Example C | 0 | 0 | 3 | 5 | 15 |
| Comp. Agent I HCM | 30 | 40 | 90 | 100 | 100 |
| Comp. Agent II BCM-HCl | 0 | 5 | 10 | 18 | 35 |
| Comp. Agent III benomyl | 0 | 0 | 5 | 12 | 25 |
| infested untreated plants | 100 | 100 | 100 | 100 | 100 |

EXAMPLE III

Tomato plants in the grown-up three-leaf stage were infested with conidia of *Cladosporium fulvum* causing leaf mould, and placed in a chamber having a temperature of 25° C and a relative humidity of 100%. After 24 hours the plants were transferred to a green-house having a temperature of 23°-25° C and a humidity of 90-95%.

After a time of infestation of 7 days the plants were sprayed to the drip off with the wettable powders and comparative agents specified in Example I, the concentrations applied being 250, 125, 60 and 30 mg of active compound per liter of spray liquor.

After drying of the coating containing the active ingredient the plants were placed again in the greenhouse and after a time of incubation of 21 days they were examined to determine the degree of infestation. It is expressed in % of infested leaf surface, relative to untreated infested control plants = 100%. The results are indicated in Table III.

TABLE III

| Formulation of | % of leaf surface infested by Cladosporium with mg of active compound per liter of spray liquor | | | |
|---|---|---|---|---|
| | 250 | 125 | 60 | 30 |
| Example A | 0 | 0 | 8 | 15 |
| Example B | 0 | 0 | 5 | 10 |
| Example C | 0 | 0 | 5 | 10 |
| Comp. Agent I BCM | 10 | 23 | 28 | 48 |
| Comp. Agent II BCM-HCl | 0 | 10 | 15 | 28 |
| Comp. Agent III benomyl | 0 | 0 | 8 | 17 |
| untreated infested plants | 100 | 100 | 100 | 100 |

EXAMPLE IV

Rice plants in the 4 leaf stage were sprayed to the drip off with aqueous suspensions of the compounds of Examples 1 and 3 in concentration of 500, 250, 120, 60 and 30 mg of active compound per liter of spray liquor. After drying of the coating the plants were uniformly sprayed with a spore suspension of *Piricularia oryzae* and placed for 48 hours in a dark chamber at 25° C and 100% of relative humidity. The plants were then kept in a greenhouse at 25° C and 85% of relative humidity and 14 days after inoculation they were examined to determine the degree of infestation with *Piricularia oryzae* by visual inspection as in the preceding example. Benomyl was used as comparative agent.

The results listed in Table IV show that the compounds of the invention are superior to benomyl in their fungicidal activity.

TABLE IV

| Compound of Example | % infested leaf surface with mg/l of spray liquor | | | | |
|---|---|---|---|---|---|
| | 500 | 250 | 120 | 60 | 30 |
| 1 | 0 | 0 | 3 | 5 | 10 |
| 3 | 0 | 0 | 0 | 3 | 5 |
| benomyl | 0 | 5 | 10 | 15 | 20 |
| untreated | 100 | 100 | 100 | 100 | 100 |

EXAMPLE V

Vicia faba plants 14 days old were sprayed to the drip off with aqueous suspensions of the compounds of Example 1 and 3, the concentrations of active ingredient being 500, 250, 120, 60 and 30 mg per liter of spray liquor. 4 to 6 hours after spraying the plants were inoculated with a spore suspension of *Botrytis cinerea* and then placed for 4 days in a chamber at 20° C and 100% of relative humidity. Thereafter the plants were examined by visual inspection to determine the degree of infestation as in the preceding example.

The results summarized in Table V show the superior fungicidal effect of the compounds of the invention in comparison to benomyl.

TABLE V

| Compound of | % infested leaf surface with mg/l of active ingredient | | | | |
|---|---|---|---|---|---|
| Example | 500 | 250 | 120 | 60 | 30 |
| 1 | 0 | 0 | 3 | 5 | 15 |
| 3 | 0 | 0 | 3 | 5 | 10 |
| benomyl | 3 | 5 | 10 | 15 | 25 |
| untreated | 100 | 100 | 100 | 100 | 100 |

EXAMPLE VI

In a field test 4 apple trees each of the type Jonathan (6 year old plantation of shrubby trees on base EM IX) were treated with aqueous suspensions of the compounds of Examples 5 and 4 against apple mildew (*Podosphaera leucotricha*). The plantation was regularly infested heavily with apple mildew. The applied spray liquor contained 0.025 and 0.0375%, respectively, of active compound. The comparative agent was benomyl used in the same concentrations. The suspensions were applied with a Holder portable sprayer under a pressure of 5 atmospheres gauge. Each tree was sprayed with ½ liter of spray liquor (shortly after sprouting of the leaves) and with 1 liter (when the leaves had fully developed). The trees were treated 5 times during the main period of infestation. The test results were evaluated in the middle of July. To this end the leaves on 80 approximately equally long main shoots were counted and subdivided in 4 classes of infestation according to BBA (Biologische Bundesanstalt of Federal Republic of Germany) scheme (class 1 meaning free from infestation, class 2 comprising the leaves with individual patches of mildew, class 3 comprising the leaves of which half of the surface is infested while the leaves of which more than half of the surface is infested belong to class 4.)

The test results listed in Table VI show that the compounds of the invention had a much better fungicidal effect than benomyl.

TABLE VI

| compound | Concentration of active ingredient wt % | number of leaves in class | | | | mean degree of infestation | % infestation in classes 2 to 4 |
|---|---|---|---|---|---|---|---|
| | | 1 | 2 | 3 | 4 | | |
| Ex. 5 | 0.025 | 391 | 203 | 59 | 6 | 1.5 | 40.7 |
| | 0.0375 | 489 | 153 | 40 | 0 | 1.35 | 28.3 |
| Ex. 4 | 0.025 | 357 | 236 | 98 | 10 | 1.65 | 49.1 |
| | 0.0375 | 437 | 198 | 31 | 3 | 1.4 | 34.7 |
| benomyl | 0.025 | 218 | 270 | 171 | 32 | 2.05 | 68.5 |
| | 0.0375 | 305 | 207 | 145 | 25 | 1.84 | 55.3 |
| untreated | | 66 | 197 | 236 | 184 | 2.8 | 90.5 |

EXAMPLE VII

In an apple plantation heavily infested with apple scab (*Venturia inaequalis*) 4 apple trees each of the type Golden Delicious (16 year old trees on base EM IX) were treated with aqueous suspensions of the compounds of Examples 5 and 4, the concentration of active compound being 0.025 and 0.0375% by weight. As comparative agents benomyl was used in the same concentrations and orthocid 50 [N-(trichloromethylthio)-3a4,7,-7a-tetrahydrophthalimide] in the recommended maximum concentration of 0.1% by weight of active ingredient. The aqueous suspensions were applied with a Holder high pressure applicator under a pressure of 20 atmospheres. Each tree was treated with about 5 liters of spray liquor (corresponding to 2,000 liters per hectare). The trees were treated 8 times during the vegetation period.

To determine the fungicidal effect the individual leaves were examined and divided in two classes, class 1 leaves being free from apple scab and class 2 leaves being infested with apple scab (corresponding to BBA scheme).

Table VII shows the fungicidal superiority of the compounds of the invention over benomyl and orthocid.

TABLE VII

| Compound of | concentration of active ingredient wt. % | number of leaves in class | | percent of infested leaves |
|---|---|---|---|---|
| | | 1 | 2 | |
| Example 5 | 0.025 | 617 | 44 | 6.7 |
| | 0.0375 | 624 | 36 | 5.5 |
| Example 4 | 0.025 | 603 | 55 | 9.1 |
| | 0.0375 | 601 | 46 | 7.1 |
| benomyl | 0.025 | 573 | 86 | 13.1 |
| | 0.0375 | 581 | 68 | 10.5 |
| orthocid | 0.1 | 524 | 107 | 17.0 |
| untreated | | 237 | 383 | 61.7 |

EXAMPLE VIII 14 days old Vicia faba plants were sprayed to the drip off with aqueous suspensions of formulations according to Example K containing as active ingredient compounds of Example 2, 7 and 8, respectively, in concentrations of 500, 250 and 120 mg each per liter. 4 to 6 hours after application of the spray liquor the plants were inoculated with a spore suspension of *Botrytis cinerea* and the infested plants were kept for 4 days in a chamber at 20° C and 100% of relative humidity. After that time the plants were examined by visual inspection to determine the degree of infestation as in Example I. The tests were repeated 4 times. Benomyl was used as comparative agent.

TABLE VIII

| Compound | % infested leaf surface with mg of active ingredient/liter | | |
|---|---|---|---|
| | 500 | 250 | 120 |
| 8 | 0 | 5 | 5 |
| 2 | 5 | 10 | 15 |
| 7 | 0 | 3 | 3 |
| benomyl | 5 | 10 | 15 |
| untreated | 100 | 100 | 100 |

EXAMPLE IX

Rice plants in the 4 leaf stage were sprayed to the drip off with formulations according to Example K containing as active ingredient the compounds of Example 2, 7, and 8 in a concentration of 500, 250 and 120 mg each per liter of spray liquor. After drying of the coating containing the active compound the plants were uniformly sprayed with a spore suspension of *Piricularia oryzae* and placed for 48 hours in a dark chamber at 25° C and 100% of relative humidity. The plants were then transferred to a greenhouse at 25° C and 85% of relative humidity and 14 days after inoculation they were examined by visual inspection to determine the degree of infestation as in Example I. The tests were repeated 4 times. Benomyl was used as comparative agent.

TABLE IX

| Compound | % infested leaf surface with mg of active compound/liter | | |
|---|---|---|---|
| | 500 | 250 | 120 |
| 8 | 0 | 3 | 3 |
| 2 | 0 | 3 | 5 |
| 7 | 0 | 3 | 3 |
| benomyl | 3 | 10 | 15 |
| untreated | 100 | 100 | 100 |

We claim:

1. A water insoluble compound of the formula $$\text{(benzimidazole)}-C-NH-COOR \cdot HO\underset{\underset{O}{\|}}{\overset{\overset{O}{\|}}{S}}-B \quad \text{II}$$

in which R is alkyl having 1–4 carbon atoms and B is alkyl, alkenyl, alkoxy each having from 10 to 20 carbon atoms, alkylphenyl, alkylnaphthyl, or alkoxy phenyl or mixtures thereof each having from 10 to 20 carbon atoms.

2. A compound as claimed in claim 1, wherein B is a hydrocarbon radical having 12 to 18 carbon atoms.

3. A compound as claimed in claim 1, wherein B is an alkylphenyl radical having 12 to 18 carbon atoms.

4. The compound of claim 1, wherein B is a dodecylphenyl radical.

5. A water-insoluble compound of the formula $$\text{(benzimidazole)}-C-NH-COOR \cdot HO\underset{\underset{O}{\|}}{\overset{\overset{O}{\|}}{S}}-B$$

in which R is alkyl having 1 to 4 carbon atoms and B is alkyl having from 10 to 20 carbon atoms.

6. A water-insoluble compound of the formula $$\text{(benzimidazole)}-C-NH-COOR \cdot HO\underset{\underset{O}{\|}}{\overset{\overset{O}{\|}}{S}}-B$$

in which R is alkyl having 1 to 4 carbon atoms and B is alkoxy having 12 to 18 carbon atoms.

7. A fungicidal composition containing as an active ingredient an effective amount of a water insoluble compound of the formula $$\text{(benzimidazole)}-C-NH-COOR \cdot HO\underset{\underset{O}{\|}}{\overset{\overset{O}{\|}}{S}}-B \quad \text{II}$$

in which R is alkyl having 1–4 carbon atoms and B is alkyl, alkenyl, alkoxy each having from 10–20 carbon atoms, alkylphenyl, alkylnaphthyl, or alkoxy phenyl or mixtures thereof each having from 10 to 20 carbon atoms in combination with a fungicidal carrier.

8. A fungicidal composition as claimed in claim 7, containing 2 to 95% of a compound of formula II 9. A fungicidal composition as claimed in claim 7 in the form of an emulsion concentrate containing 5 to 30% of a compound of formula II in combination with high boiling solvents and non ionic emulsifiers.

10. A fungicidal composition as claimed in claim 9, containing 10 to 20% of the compound of formula II.

11. A fungicidal composition as claimed in claim 7 suitable for ultra low volume application containing 5 to 40% of the compound of formula II in combination with high boiling solvents.

12. A fungicidal composition as claimed in claim 7 suitable for seed treatment containing 5 to 40% of a compound of formula II in a solvent.

13. Process for combating fungus diseases in plants which comprises treating the plants with an effective amount of a compound as claimed in claim 1.

* * * * *